(12) United States Patent
Wakamiya et al.

(10) Patent No.: US 8,329,103 B2
(45) Date of Patent: Dec. 11, 2012

(54) SAMPLE ANALYZER AND METHOD FOR ANALYZING SAMPLES

(75) Inventors: Yuji Wakamiya, Hyogo (JP); Tomohiro Okuzaki, Hyogo (JP); Hisato Takehara, Hyogo (JP)

(73) Assignee: Sysmex Corporation, Kobe (JP)

( * ) Notice: Subject to any disclaimer, the term of this patent is extended or adjusted under 35 U.S.C. 154(b) by 626 days.

(21) Appl. No.: 12/284,130

(22) Filed: Sep. 18, 2008

(65) Prior Publication Data

US 2009/0081794 A1   Mar. 26, 2009

(30) Foreign Application Priority Data

Sep. 20, 2007   (JP) ................................ 2007-243381

(51) Int. Cl.
| | |
|---|---|
| *G01N 35/00* | (2006.01) |
| *G01N 35/02* | (2006.01) |
| *G01N 31/00* | (2006.01) |
| *G01N 21/00* | (2006.01) |
| G01N 33/50 | (2006.01) |
| G01N 33/00 | (2006.01) |
| G06F 15/00 | (2006.01) |
| G01C 9/00 | (2006.01) |

(52) U.S. Cl. ................ 422/67; 422/63; 422/64; 422/65; 422/68.1; 436/43; 436/47; 436/50; 702/19; 702/22; 702/30; 702/127; 702/150

(58) Field of Classification Search ........................ None
See application file for complete search history.

(56) References Cited

U.S. PATENT DOCUMENTS

| | | | | |
|---|---|---|---|---|
| 7,390,460 | B2 * | 6/2008 | Osawa et al. | 422/65 |
| 2007/0118294 | A1 * | 5/2007 | Jacobs | 702/19 |
| 2007/0148042 | A1 | 6/2007 | Ootani et al. | |
| 2008/0063570 | A1 * | 3/2008 | Fujino et al. | 422/99 |
| 2009/0206234 | A1 * | 8/2009 | Okuda et al. | 250/201.2 |

FOREIGN PATENT DOCUMENTS

JP           07-280815           10/1995

\* cited by examiner

*Primary Examiner* — In Suk Bullock
*Assistant Examiner* — Jennifer Wecker
(74) *Attorney, Agent, or Firm* — Brinks Hofer Gilson & Lione

(57) ABSTRACT

An sample analyzer, which enables to confirm an analysis remaining time for each sample and a total analysis remaining time for all samples set in the analyzer, so that time management for both each sample and all samples can be easily performed, is disclosed. Specifically, an analyzing unit analyzes a sample by executing an analysis sequence including a predetermined number of analyzing steps, and an control device calculates an analysis remaining time for each sample based on the number of analyzing steps. Control device acquires a total analysis remaining time by calculating the analysis remaining time for the sample in which sample information is lastly inputted. The display member displays the analysis remaining time and the total analysis remaining time.

11 Claims, 11 Drawing Sheets

| | Cuvette information | | |
|---|---|---|---|
| ID | 123456789012345 | Vol | 30.0 uL |
| Test | HBsAg | ✓R1 | 20.0 uL |
| | | R2 | 20.0 uL |
| Pos | 7 (Primary reaction member) | R3 | 20.0 uL |
| Stat | Sample stirring completed | R4 | 20.0 uL |
| | | R5 | 20.0 uL |
| Left | 10 min. | ✓Sample | 10.0 uL |
| | | Dilution | 0.0 uL |

FIG. 11

SAMPLE ANALYZER AND METHOD FOR ANALYZING SAMPLES

REFERENCE TO THE RELATED APPLICATIONS

This application claims priority under 35 U.S.C. §119 to Japanese Patent Application No. JP2007-243381 filed on Sep. 20, 2007, the entire content of which is hereby incorporated by reference.

FIELD OF THE INVENTION

The present invention relates to a sample analyzer and a method for analyzing samples.

BACKGROUND

The sample analyzers for measuring items associated with various aspects of the sample such as blood and urine are being used in hospitals and examination centers. Among such sample analyzers, a great amount of samples are processed using a plurality of types of reagents in immune analyzers and blood coagulation analyzers.

Samples that require measurement result to be urgently notified to determine the treatment policy at an early stage or to determine the necessity of other examinations coexist in the samples processed by the sample analyzer. In this case, however, it is difficult to understand how much time is required to obtain the measurement result of the target sample in the conventional sample analyzer.

Thus, an automatic sample processing device capable of automatically calculating when a final processing result of a specific sample can be obtained, and displaying the calculated time information has been proposed. In the device described in Patent Publication JP H07-280815, identification information of the sample to be set is input to the calculation, control, and display devices through keyboard operation when setting the sample in the device. When the desired sample is specified, in the calculation, control, and display devices, it is determined that which station of a plurality of stations the sample is located, and the time until analysis is terminated is calculated and displayed from the station where the sample is currently positioned.

According to the device described in Patent Publication JP H07-280815, the remaining time until the analysis of the specific sample is terminated can be understood, but the time until the analysis of all the samples scheduled to be analyzed in the relevant sample analyzer is terminated cannot be understood, and thus the time management in the sample analyzer cannot be adequately performed.

SUMMARY OF THE INVENTION

A first aspect of present invention is a sample analyzer comprising: an order accepter for accepting an analysis order indicating an analysis content; an analyzing unit for analyzing a sample according to the analysis order accepted by the order accepter; a sample specifier for specifying a sample; a first acquirer for acquiring an analysis remaining time required until an analysis of the specified sample ends or an analysis end time that an analysis of the specified sample ends; a second acquirer for acquiring a total analysis remaining time required until analyses of all samples by the analyzing unit end or a total analysis end time that analyses of all samples by the analyzing unit end; a display; and a display controller for controlling the display to display the analysis remaining time or the analysis end time acquired by the first acquirer, and the total analysis remaining time or the total analysis end time acquired by the second acquirer.

A second aspect of present invention is a sample analyzer comprising: an analyzing unit; and a computer system, including a display and a memory under control of a processor, the memory storing instructions enabling the processor to carry out operations, comprising: a step of accepting an analysis order indicating an analysis content; a step of executing an analysis of a sample by the analyzing unit according to the analysis order; a step of accepting a specification of a sample; a step of acquiring an analysis remaining time required until an analysis of the sample specified by the specification ends or an analysis end time that an analysis of the sample specified by the specification ends; a step of acquiring a total analysis remaining time required until analyses of all samples by the analyzing unit end or a total analysis end time that analyses of all samples by the analyzing unit end; and a step of displaying the analysis remaining time or the analysis end time, and the total analysis remaining time or the total analysis end time on the display.

A third aspect of present invention is a method for analyzing samples comprising: a step of accepting an analysis order indicating an analysis content; a step of analyzing a sample according to the accepted analysis order; a step of accepting a specification of a sample; a step of acquiring an analysis remaining time required until an analysis of the sample specified by the specification ends or an analysis end time that an analysis of the sample specified by the specification ends; a step of acquiring a total analysis remaining time required until analyses of all samples end or a total analysis end time that analyses of all samples end; and a step of displaying the acquired analysis remaining time or the analysis end time, and the acquired total analysis remaining time or the total analysis end time.

BRIEF DESCRIPTION OF THE DRAWINGS

FIG. 11 is a view showing one example of a cuvette information screen.

DETAILED DESCRIPTION OF THE INVENTION

The preferred embodiments of the present invention will be described in detail hereinafter with reference to the drawings.

[Overall Configuration of Apparatus]

Figure 1:
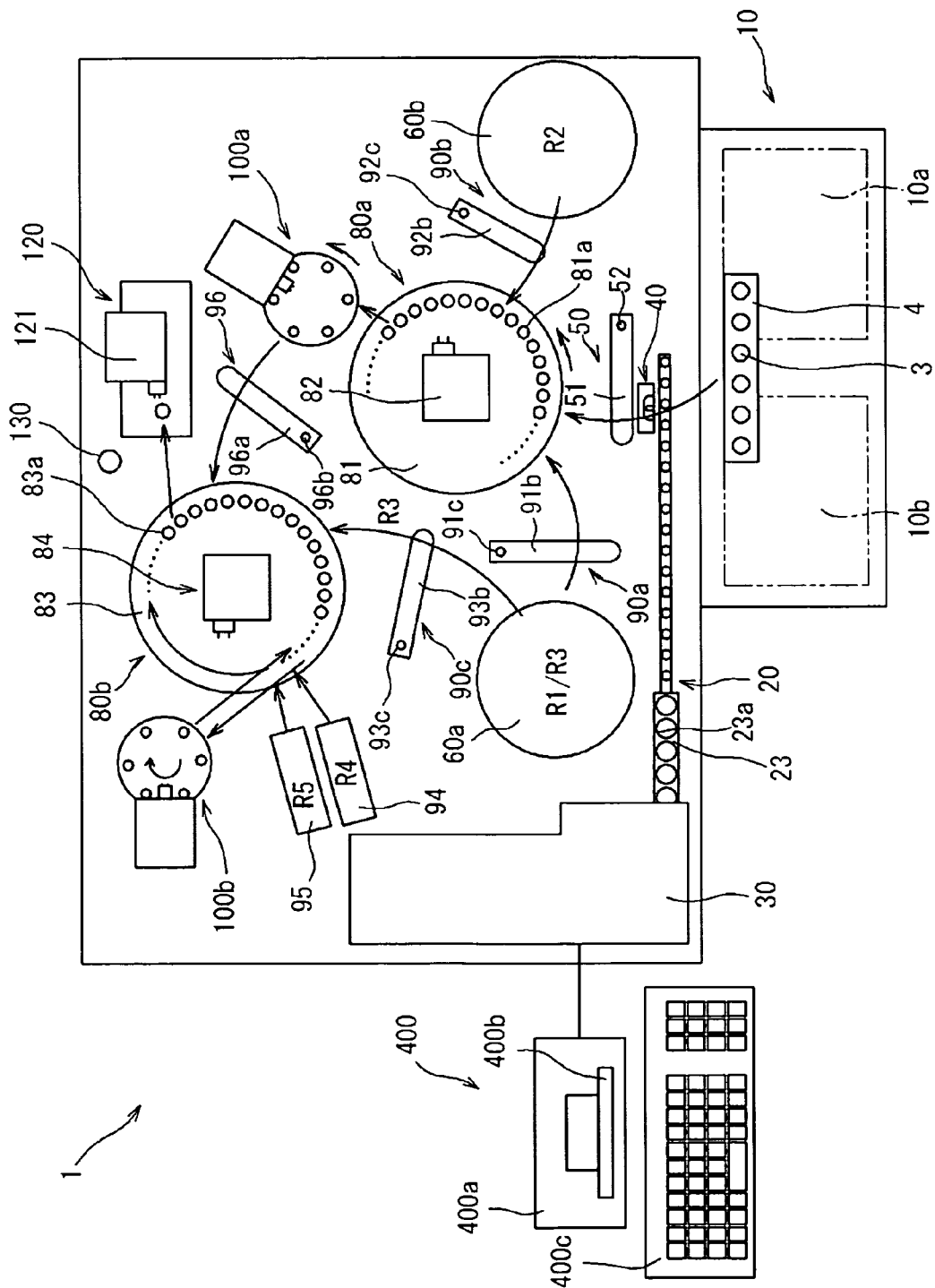
FIG. 1 is a plan view showing an overall configuration of one embodiment of a sample analyzer of the present invention.

FIG. 1 is a plan explanatory view showing an overall configuration of an immune analyzer (sample analyzer) according to one embodiment of the present invention.

Figure 2:
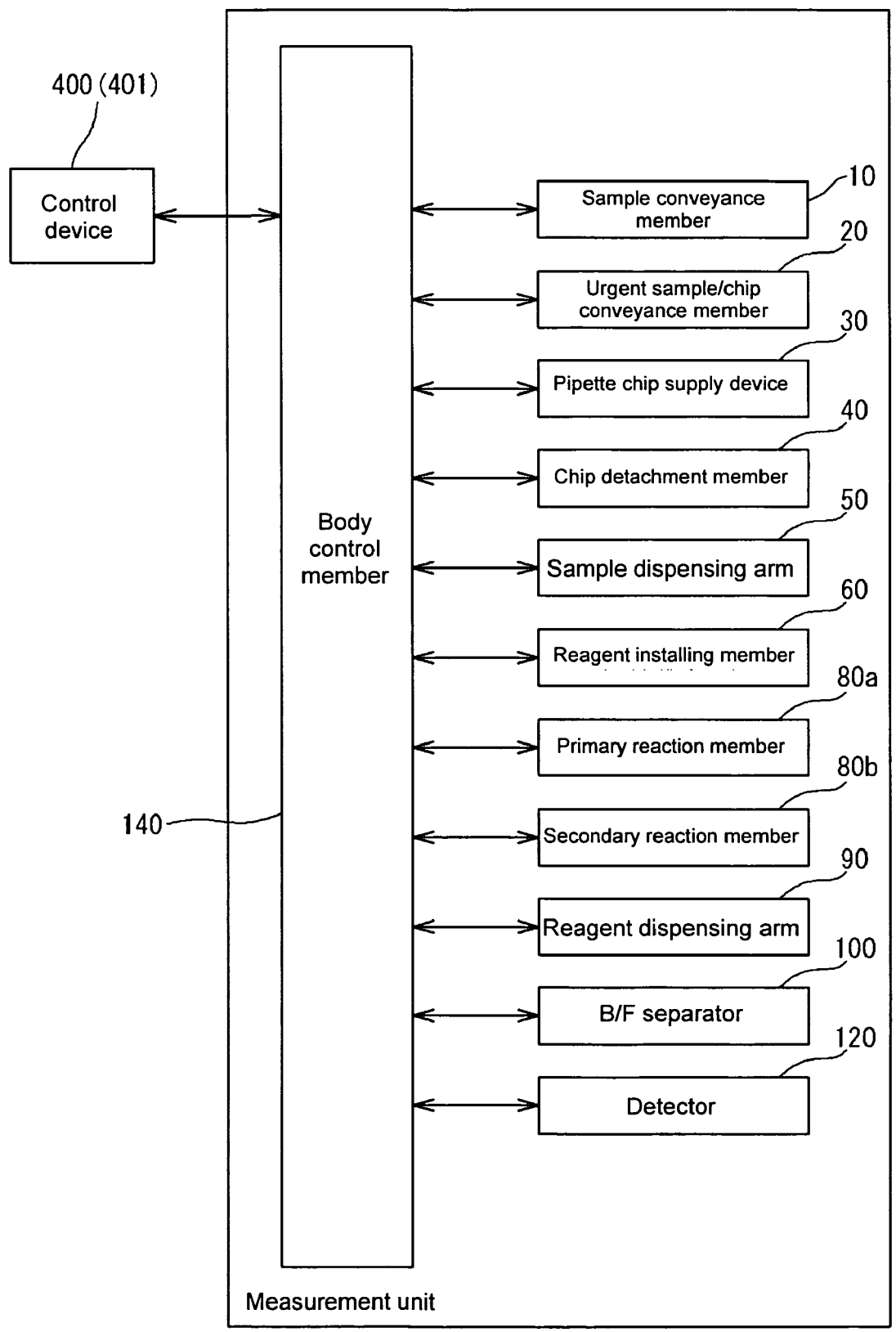
FIG. 2 is a block diagram showing a configuration of a measurement unit in the immune analyzer shown in FIG. 1.

An immune analyzer 1 according to one embodiment of the present invention is an apparatus for carrying out examinations on various items such as hepatitis B, hepatitis C, tumor marker, and thyroid hormone by using sample such as blood. As schematically shown in FIG. 1, the immune analyzer 1 is mainly configured by a measurement unit (analyzing unit) including a sample conveyance member (sampler) 10, an urgent sample/chip conveyance member 20, a pipette chip supply device 30, a chip detachment member 40, a sample dispensing arm 50, reagent installing members 60a and 60b, a primary reaction member 80a and a secondary reaction member 80b, reagent dispensing arms 90a, 90b, and 90c, a primary B/F separator 100a and a secondary B/F separator 100b, a detector 120, and a control member 140 (see FIG. 2) for performing operation control of mechanisms such as the sample conveyance member (sampler) 10 and the sample dispensing arm 50; and a control device 400 (see FIG. 3) serving as a data processing unit electrically connected to the measurement unit. In the immune analyzer 1 according to the present embodiment, the disposable pipette chip is changed every time aspiration and discharge of sample are performed in order to prevent the sample such as blood aspirated and discharged by the sample dispensing arm 50 from mixing with other samples.

In the immune analyzer 1, magnetic particles (R2 reagent) are bonded to a trapping antibody (R1 reagent) bonded to an antigen contained in a sample such as blood, which is the measuring object, and thereafter, the bound antigen, the trapping antibody, and the magnetic particles are attracted to a magnet of the primary B/F (Bound Free) separator 100a to remove the R1 reagent containing non-reactive (free) trapping antibody. A labeling antibody (R3 reagent) is bonded to the antigen bound with the magnetic particles, and thereafter, the bound magnetic particles, the antigen, and the labeling antibody are attracted to a magnet of the secondary B/F separator 100b to remove the R3 reagent containing non-reactive (free) labeling antibody. Furthermore, a dispersion liquid (R4 reagent) is added, and a luminescent substrate (R5 reagent) that emits light in the reaction process with the labeling antibody is added, and thereafter, a light emission amount generated through the reaction of the labeling antibody and the luminescent substrate is measured. Through such processes, the antigen contained in the sample that bonds with the labeling antibody is quantitatively measured. R4 may not be added depending on the analyzing item.

[Configuration of Control Device]

The control device 400 is configured by a personal computer 401 (PC) or the like, and includes a control member 400a, a display member 400b, and a keyboard 400c, as shown in FIG. 1. The control member 400a has a function of instructing the start of measurement operation to the measurement unit, and analyzing the optical information of the sample obtained in the measurement unit. The display member 400b is provided to display the analysis result obtained by the control member 400a, and to display the measurement progress screen etc. to be hereinafter described.

Figure 3:
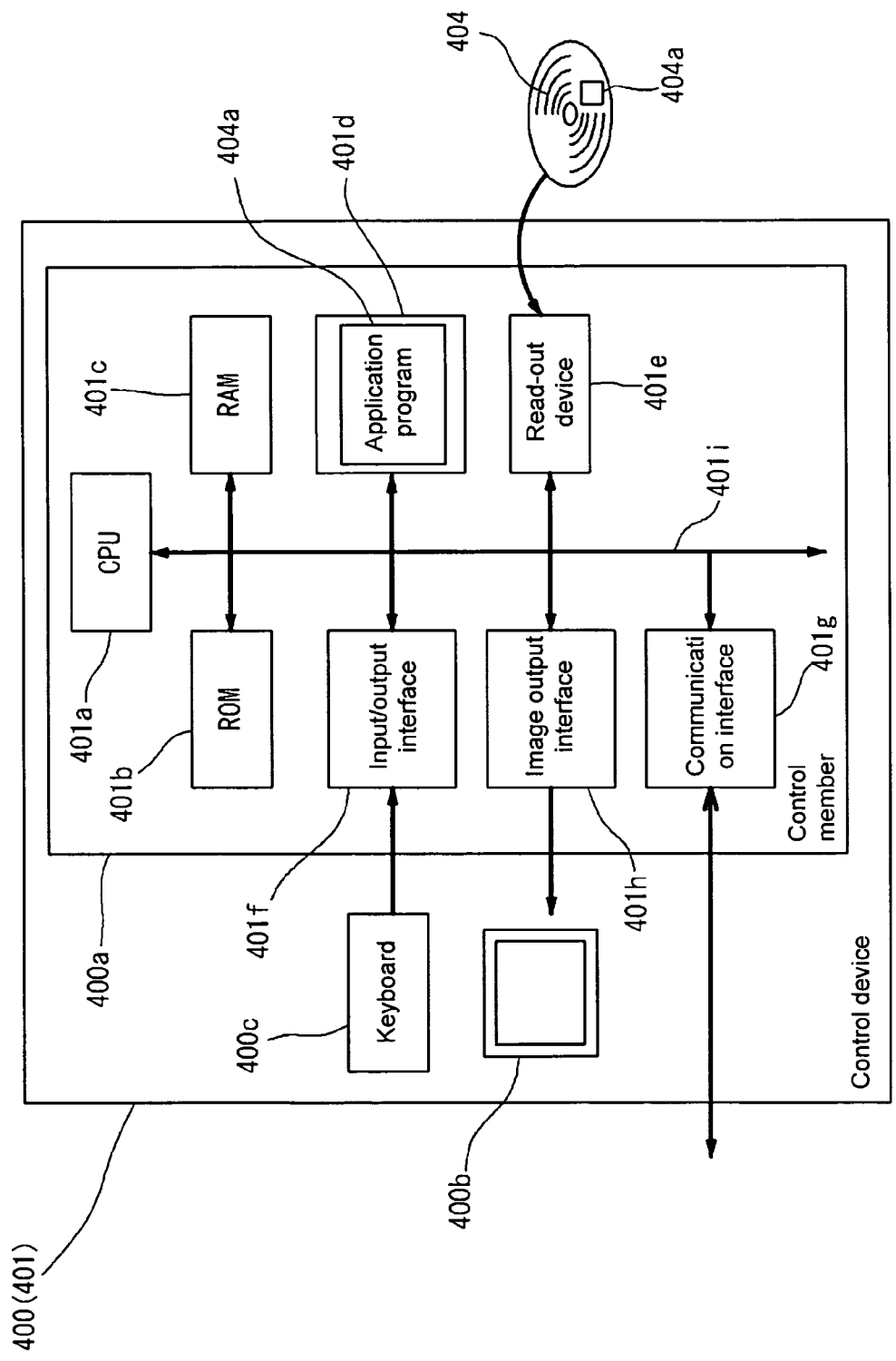
FIG. 3 is a block diagram of a control device in the immune analyzer shown in FIG. 1.

The configuration of the control device 400 will now be described. As shown in FIG. 3, the control member 400a is mainly configured by a CPU 401 a, a ROM 401b, a RAM 401c, a hard disc 401d, a read-out device 401e, an input/output interface 401 f, a communication interface 401 g, and an image output interface 401h. The control member 400a is provided to acquire the analysis remaining time required until sample analysis is terminated, and display the analysis remaining time on the display member 400b.

The CPU 401a, the ROM 401b, the RAM 401c, the hard disc 401d, the read-out device 401e, the input/output interface 401f, the communication interface 401g, and the image output interface 401h are connected by a bus 401i.

The CPU 401a can execute computer programs stored in the ROM 401b and the computer programs loaded in the RAM 401c. The computer 401 serves as the control device 400 when the CPU 401a executes an application program 404a, as hereinafter described.

The ROM 401b is configured by mask ROM, PROM, EPROM, EEPROM, or the like, and is recorded with computer programs to be executed by the CPU 401a, data used for the same, or the like.

The RAM 401c is configured by SRAM, DRAM, or the like. The RAM 401c is used to read out the computer programs recorded on the ROM 401b and the hard disc 401d. The RAM 401c is used as a work region of the CPU 401a when executing the computer programs.

The hard disc 401d is installed with various computer programs to be executed by the CPU 401a such as operating system and application program, as well as data used in executing the computer program. The application program 404a for registering the measurement order, acquiring the analysis remaining time, and displaying the same according to the present embodiment is also installed in the hard disc 401d.

The read-out device 401e is configured by flexible disc drive, CD-ROM drive, DVD-ROM drive, or the like, and is able to read out computer programs and data recorded on a portable recording medium 404. The application program 404a according to the present embodiment is stored in the portable recording medium 404, wherein the computer 401 can read out the application program 404a from the portable recording medium 404, and install the application program 404a to the hard disc 401d.

The application program 404a is not only provided by the portable recording medium 404, but also provided through communication line (wired or wireless) from external devices communicatably connected with the computer 401 through the communication line. For instance, the application program 404a may be stored in the hard disc of the server computer on the Internet, so that the computer 401 can access the server computer to download the application program 404a and install the application program 404a to the hard disc 401d.

Operating system providing graphical user interface environment such as Windows (registered trademark) manufactured and sold by U.S. Microsoft Co. is installed in the hard disc 401d. In the following description, the application program 404a according to the present embodiment is assumed to be operated on the operating system.

The input/output interface 401f is configured by serial interface such as USB, IEEE1394, RS-232C; parallel interface such as SCSI, IDE, IEEE1284; analog interface such as D/A converter, A/D converter, or the like. The keyboard 400c is connected to the input/output interface 401f, so that the user can input data to the computer 401 by using the keyboard 400c.

The communication interface 401g is, for example, Ethernet (registered trademark) interface. The computer 401 transmits and receives data with the measurement unit by using a predetermined communication protocol by means of the communication interface 401g.

The image output interface 401h is connected to the display member 400b configured by LCD, CRT, or the like, and is configured to output an image signal corresponding to the image data provided from the CPU 401a to the display member 400b. The display member 400b displays the image (screen) according to the input image signal.

[Configuration of each Mechanism of the Immune Analyzer]

The configuration of each mechanism of the immune analyzer 1 may appropriately adopt a known configuration, and will be briefly described below.

The sample conveyance member 10 is configured to convey a rack 4 mounted with a plurality of test tubes 3 containing the sample to a position corresponding to an aspiration position of the sample dispensing arm 50. The sample conveyance member 10 includes a rack set section 10a for setting the rack 4 mounted with the test tube 3 containing un-processed sample, and a rack storage section 10b for storing the rack 4 mounted with the test tube 3 containing dispense processed sample. When the test tube 3 containing the non-processed sample is conveyed to the position corresponding to the aspiration position of the sample dispensing arm 50, the sample such as blood in the test tube 3 is aspirated by the sample dispensing arm 50, and the rack 4 mounted with the relevant test tube 3 is stored in the rack storage section 10b.

The urgent sample/chip conveyance member 20 is configured to convey the test tube 3 containing urgent sample that needs to be cut into the order of the samples being conveyed by the sample conveyance member 10 for examination to an attachment position of the sample dispensing arm 50.

The pipette chip supply device 30 has a function of mounting a pipette chip on a chip installing section 23a of a conveyance rack 23 of the urgent sample/chip conveyance member 20 one at a time.

The chip detachment member 40 is provided to detach the pipette chip attached to the sample dispensing arm 50 to be hereinafter described.

The sample dispensing arm 50 has a function of dispensing the sample in the test tube 3 conveyed to the aspiration position by the sample conveyance member 10 into a cuvette (not shown) held at a holder 81a of a rotatable table 81 of the primary reaction member 80a to be hereinafter described. The sample dispensing arm 50 is configured so that an arm 51 can be turned with a shaft 52 as a center and moved in an up and down direction (Z-direction). A nozzle for aspirating and discharging sample is provided at the edge of the arm 51, and a pipette chip conveyed by a conveyance rack (not shown) of the urgent sample/chip conveyance member 20 is attached to the edge of the nozzle.

The reagent installing member 60a is installed with a reagent container containing the R1 reagent including trapping antibody and a reagent container containing the R3 reagent including labeling antibody.

The reagent installing member 60b is installed with a reagent container containing the R2 reagent including magnetic particles.

The primary reaction member 80a is provided to rotatably transport the cuvette held at the holder 81a of the rotatable table 81 by a predetermined angle for every predetermined period (20 seconds in the present embodiment), and to stir the sample, the R1 reagent, and the R2 reagent in the cuvette. That is, the primary reaction member 80a is provided to react the R2 reagent having magnetic particles with the antigen in the sample in the cuvette. The primary reaction member 80a is configured by the rotatable table 81 for conveying the cuvette containing the sample, the R1 reagent, and the R2 reagent in the rotating direction, and a container conveyance section 82 for stirring the sample, the R1 reagent, and the R2 reagent in the cuvette and conveying the cuvette containing the stirred sample, the R1 reagent, and the R2 reagent to the primary B/F separator 100a to be hereinafter described.

The container conveyance section 82 is rotatably installed at the center of the rotatable table 81. The container conveyance section 82 has a function of gripping the cuvette held at the holder 81a of the rotatable table 81 and stirring a specimen in the cuvette. The container conveyance section 82 also has a function of conveying the cuvette containing the specimen obtained by stirring and incubating the sample, the R1 reagent, and the R2 reagent to the primary B/F separator 100a.

The reagent dispensing arm 90a has a function of aspirating the R1 reagent in the reagent container installed in the reagent installing member 60a, and dispensing the aspirated R1 reagent into the cuvette of the primary reaction member 80a. The reagent dispensing arm 90a is configured so that an arm 91b can be turned with a shaft 91c as a center and moved in an up and down direction. A nozzle for aspirating and discharging the R1 reagent in the reagent container is attached to the edge of the arm 91b.

The reagent dispensing arm 90b has a function of dispensing the R2 reagent in the reagent container installed in the reagent installing member 60b into the cuvette dispensed with the sample and the R1 reagent of the primary reaction member 80a. The reagent dispensing arm 90b is configured so that an arm 92b can be turned with a shaft 92c as a center and moved in an up and down direction (Z-direction). A nozzle for aspirating and discharging the R2 reagent in the reagent container is attached to the edge of the arm 92b.

In the present embodiment, the primary B/F separator 100a is provided to separate the non-reactive R1 reagent (unnecessary component) and the magnetic particles from the specimen in the cuvette conveyed by the container conveyance section 82 of the primary reaction member 80a.

The cuvette on the B/F separator 100a separated with the non-reactive R1 reagent etc. is conveyed to a holder 83a of a rotatable table 83 of the secondary reaction member 80b by a conveyance mechanism 96. The conveyance mechanism 96 is configured so that an arm 96a having a cuvette gripping part (not shown) at the edge is turned with a shaft 96b as a center and is moved in an up and down direction (Z direction).

The secondary reaction member 80b has a configuration similar to the primary reaction member 80b, and is provided to rotatably transport the cuvette held at the holder 83a of the rotatable table 83 by a predetermined angle for every predetermined period (20 seconds in the present embodiment), and to stir the sample, the R1 reagent, the R2 reagent, the R3 reagent, the R4 reagent, and the R5 reagent in the cuvette. That is, the secondary reaction member 80b is provided to react the R3 reagent having labeling antibody with the antigen in the sample in the cuvette, and to react the R5 reagent having luminescent substrate with the labeling antibody of the R3 reagent. The secondary reaction member 80b is configured by the rotatable table 83 and a container conveyance section 84. The rotatable table 83 has function is provided for for conveying the cuvette containing the sample, the R1 reagent, the R2 reagent, the R3 reagent, the R4 reagent and the R5 reagent in the rotating direction. The container conveyance section 84 is provided for stirring the sample, the R1 reagent, the R2 reagent, the R3 reagent, the R4 reagent and the R5 reagent in the cuvette, and for conveying the cuvette containing the stirred sample to the secondary B/F separator 100b to be hereinafter described. Furthermore, the container conveyance section 84 has a function of again conveying the cuvette processed by the B/F separator 100b to the holder 83a of the rotatable table 83.

The reagent dispensing arm 90c has a function of aspirating the R3 reagent in the reagent container installed at the reagent installing member 60a and dispensing the aspirated R3 reagent into the cuvette dispensed with the sample, the R1 reagent, and the R2 reagent of the secondary reaction member 80b. The reagent dispensing arm 90c is configured so that an arm 93b can be turned with a shaft 93c as a center and moved in an up and down direction. A nozzle for aspirating and discharging the R3 reagent in the reagent container is attached to the edge of the arm 93b.

The secondary B/F separator 100b has a configuration similar to the primary B/F separator 100a, and is provided to separate the non-reactive R3 reagent (unnecessary component) and the magnetic particles from the specimen in the cuvette conveyed by the container conveyance section 84 of the secondary reaction member 80b.

An R4 reagent supply member 94 and an R5 reagent supply member 95 are respectively provided to supply the R4 reagent and the R5 reagent into the cuvette held at the holder 83a of the rotatable table 83 of the secondary reaction member 80b.

The detector 120 is provided to measure the amount of antigen contained in a sample by acquiring the light generated in the reaction process of the labeling antibody bound to the antigen of the sample performed with a predetermined process and the luminescent substrate with a photo multiplier tube. The detector 120 includes a conveyance mechanism section 121 for conveying the cuvette held at the holder 83a of the rotatable table 83 of the secondary reaction member 80b to the detector 120.

The used cuvette aspirated with the measured specimen is discarded to a dust box (not shown) arranged at the lower part of the immune analyzer 1 through a discarding hole 130.

[Overall Process]

Figure 4:
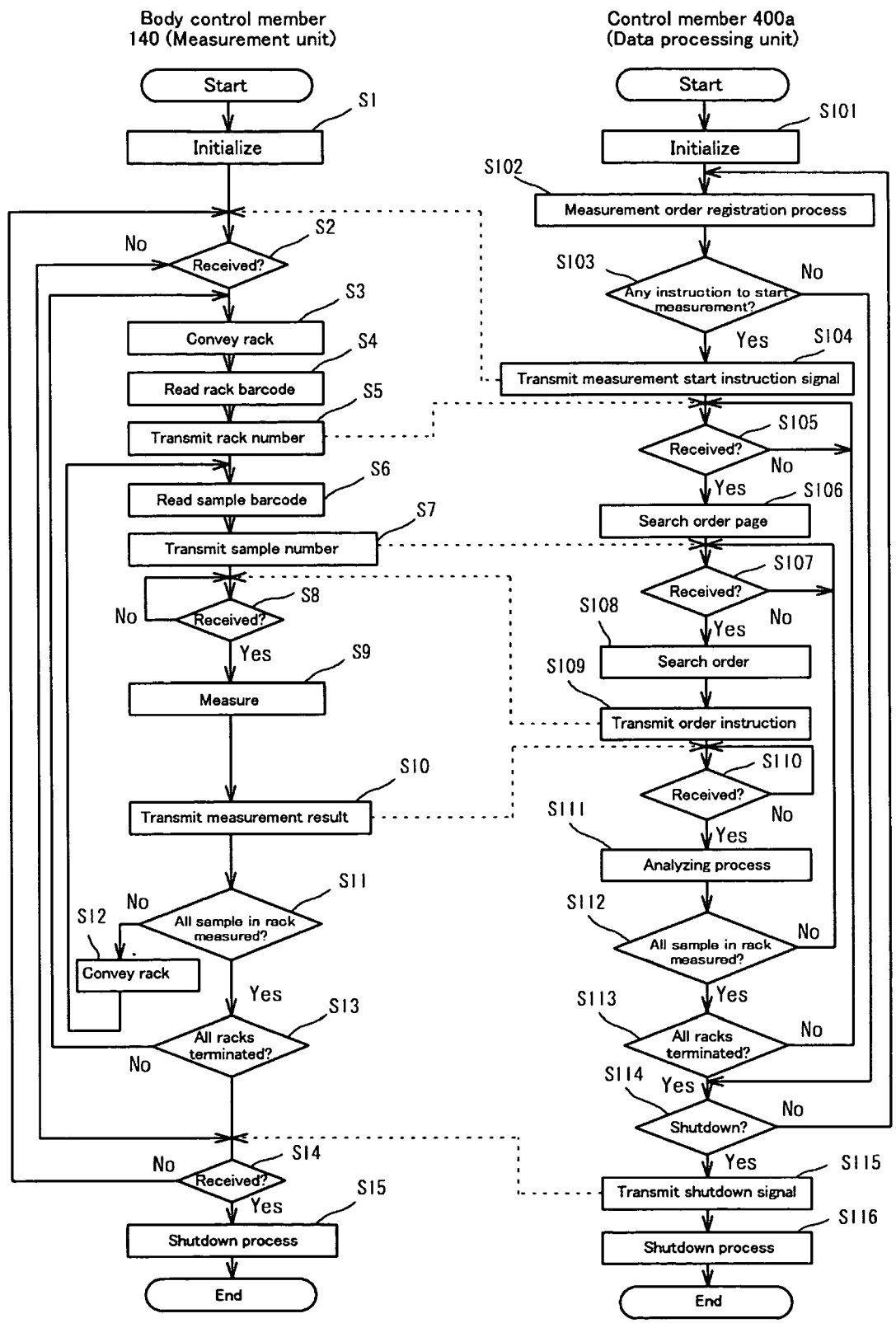
FIG. 4 is an overall flowchart of an immune analysis using the immune analyzer shown in FIG. 1.

The overall flow of the analyzing process by the immune analyzer 1 is shown in FIG. 4. In the determination in the flowchart below, if "Yes" and "No" are not shown, the downward arrow means Yes, and the right (left) arrow means No. The process described below is the process controlled by the control member 400a or the body control member 140.

First, when the power of the immune analyzer 1 is turned ON, initialization of the body control member 140 is performed (step S1). In the initialization operation, initialization of the program, return to original position of the drive portion of the immune analyzer 1, or the like are performed.

When the power of the personal computer 401 communicatably connected to the immune analyzer 1 is turned ON, initialization of the control member 400a of the personal computer 401 is performed (step S101). In the initialization operation, initialization of the program or the like are performed. After initialization is completed, order registration of the sample for performing analysis by using the immune analyzer 1 is performed (step S102). The order registration is performed by having the user input information such as sample number and measurement item (analyzing item) from the keyboard (input means) 400c, and after checking the content, having the user click the instruction button of order registration. The order registration executed by the control member 400a is stored in a storage region of the hard disc 401d.

In step S103, the control member 400a determines whether or not instruction to start the measurement is made. The control member 400a advances the process to step S104 when determining that instruction to start the measurement is made (Yes), and advances the process to step S114 when determining that instruction to start the measurement is not made (No). In step S104, the control member 400a transmits the measurement start signal to the body control member 140.

In step S2, the body control member 140 determines whether or not the measurement start signal is received. The body control member 140 advances the process to step S3 when determining that the measurement start signal is received (Yes), and advances the process to step S14 when determining that the measurement start signal is not received (No).

In step S3, the sample conveyance member 10 conveys the rack 4 mounted with a plurality of test tubes 3 containing the sample to a position corresponding to the aspiration position of the sample dispensing arm 50. The rack 4 is given a barcode recorded with information (rack number) for specifying the rack 4, and a detection means (not shown) arranged on a conveyance path for conveying the rack to a predetermined position reads the barcode (step S4). The read rack number is transmitted to the personal computer 401 side by the body control member 140 in step S5.

In step S105, the control member 400a determines whether or not the rack number is received. The control member 400a advances the process to step S106 when determining that the rack number is received (Yes).

In step S106, the control member 400a searches the order page. In other words, the control member 400a searches for the order information related to the rack number received in step S105 from the order information stored in the storage region of the hard disc 401d.

A barcode recorded with information (sample number) for specifying the sample in the test tube 3 is attached to the test tube 3 as in the rack 4, and the barcode is read by a detection means (not shown) arranged on a conveyance path for conveying the rack 4 mounted with the test tube 3 to a predetermined position (Step S6). In step S7, the read sample number is transmitted to the personal computer 401 side. The barcodes of the test tube 3 and the rack 4 may be read by different detection means or may be read by a common detection means.

In step S107, the control member 400a determines whether or not the sample number is received. The control member 400a advances the process to step S108 when determining that the sample number is received (Yes).

In step S108, the control member 400a searches the order. In other words, the control member 400a searches for the order information related to the sample number received in step S107 from the order information related to the specific rack number searched in step S106. In step S109, the control member 400a transmits the instruction of order to the body control member 140.

In step S8, the body control member 140 determines whether or not the order instruction is received. The body control member 140 advances the process to step S9 when determining that the order instruction is received (Yes).

In step S9, measurement on the ordered item is performed. The measurement result is transmitted from the body control member 140 to the personal computer 401 side (Step S10).

In step S110, the control member 400a determines whether or not the measurement result is received. The control member 400a advances the process to step S111 when determining that the measurement result is received (Yes).

In step S111, analyzing process of the measurement result transmitted from the body control member 140 side is performed. In other words, the control member 400a calculates the concentration of the antigen to be measured based on the transmitted measurement result and an analytical curve created by using a standard specimen in advance and stored in the hard disc 401d, and stores the result (analysis result). The control member 400a also outputs the analysis result.

In step S112, the control member 400a determines whether or not the measurement is performed on the samples in all of the test tubes 3 held at the rack 4. The control member 400a advances the process to step S113 when determining that the measurement is performed on the samples in all of the test tubes 3 held at the rack 4 (Yes), and returns the process to step S107 when determining that the measurement is not performed on the samples in all of the test tubes 3 held at the rack 4 (No).

In step S13, the control member 400a determines whether or not the measurement is performed on all of the racks 4. The control member 400a advances the process to step S114 when determining that the measurement is performed on all of the racks 4 (Yes), and returns the process to step S105 when determining that the measurement is not performed on all of the rack 4 (No).

In step S114, the control member 400a determines whether or not an instruction to shutdown the personal computer 401 is received. The control member 400a advances the process to step S115 when determining that the instruction to shutdown is received (Yes), and returns the process to step S103 when determining that the instruction to shutdown is not received (No).

In step S115, the control member 400a transmits a shutdown signal to the body member 140.

In step S116, the control member 400a shuts down the personal computer 401, and the process is terminated.

In step S111, the body control member 140 determines whether or not the measurement is performed on the samples in all of the test tubes 3 held at the rack 4. The body control member 140 advances the process to step S13 when determining that the measurement is performed on the samples in all of the test tubes 3 held at the rack 4 (Yes), and conveys the rack 4 by a predetermined distance (distance for the test tube containing the sample to be measured next to reach the position to be aspirated) (step S12) when determining that the measurement is not performed on the samples in all the test tubes 3 held at the rack 4 (No), and returns the process to step S6.

In step S13, the body control member 140 determines whether or not the measurement is performed on all of the racks 4. The body control member 140 advances the process to step S14 when determining that the measurement is performed on all of the racks 4 (Yes), and returns the process to step S3 when determining that the measurement is not performed on all of the rack 4 (No).

In step S14, the body control member 140 determines whether or not the shutdown signal is received. The body control member 140 advances the process to step S15 when determining that the shutdown signal is received (Yes), and returns the process to step S2 when determining that the shutdown signal is not received (No).

In step S15, the body control member 140 shuts down the immune analyzer 1, and the process is terminated.

[Measurement Process]

Figure 5:
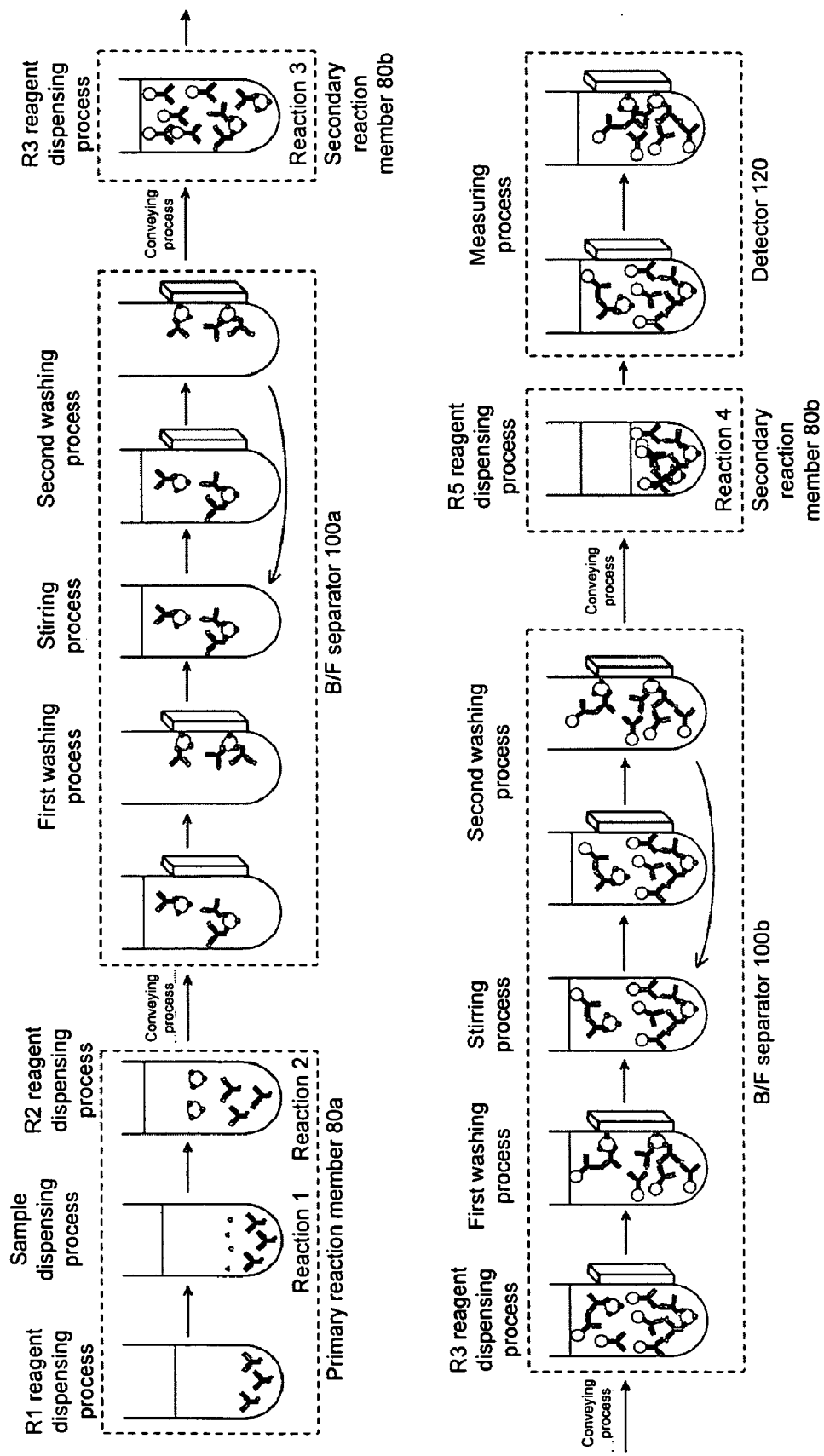
FIG. 5 is a measurement flowchart of the immune analyzer shown in FIG. 1.
Figure 6:
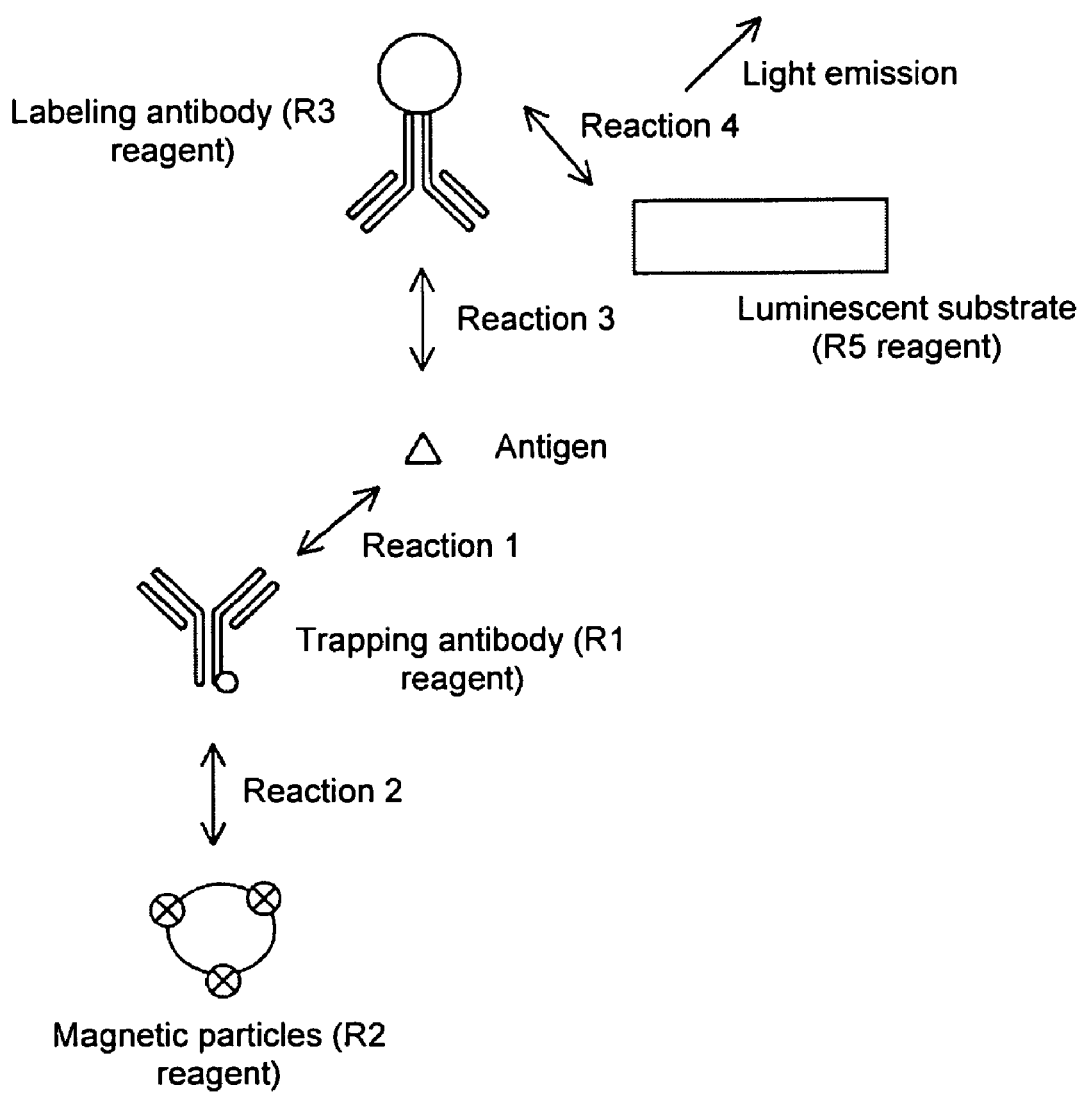
FIG. 6 is a view showing a frame format of reaction between an antigen of a sample measured in the immune analyzer shown in FIG. 1 and various reagents.

FIG. 5 is a view showing the measurement flow in step S9, and FIG. 6 is a view showing a frame format of the reaction between the antigen of the sample measured in the immune analyzer shown in FIG. 1 and various reagents.

(Cuvette Supplying Step)

First, the cuvette is conveyed to the holder 81a of the rotatable table 81 of the primary reaction member 80a by the cuvette supply member (not shown).

(R1 Reagent Dispensing Step)

After aspirating the R1 reagent in the reagent container installed in the reagent installing member 60a, the reagent dispensing arm 90a is turned towards the primary reaction member 80a side to discharge the aspirated R1 reagent into the cuvette held at the holder 81a of the rotatable table 81. As shown in FIGS. 5 and 6, the R1 reagent contains trapping antibody that binds to the antigen contained in the sample.

(Sample Dispensing Step)

After being attached with the pipette chip conveyed to the conveyance rack of the urgent sample/chip conveyance member 20, the sample dispensing arm 50 aspirates the sample such as blood from the test tube 3 mounted on the rack 4 conveyed to the aspiration position by the sample conveyance member 10. The sample dispensing arm 50 is then turned towards the primary reaction member 80a side to discharge the aspirated sample into the cuvette dispensed with the R1 reagent in the R1 reagent dispensing step. The dispensing of sample is performed for every analyzing item instructed by the order with respect to the relevant sample. In other words, dispensing of sample is performed by the number of analyzing items in the sample in which a plurality of analyzing items is instructed.

(Stirring Step of R1 Reagent and Sample)

The container conveyance section 82 of the primary reaction member 80a then stirs the cuvette containing the R1 reagent and the sample.

(Incubation Step (Reaction 1 Shown in FIGS. 5 and 6))

The stirred R1 reagent and the sample are then incubated for a predetermined time in the cuvette of the holder 81a of the rotatable table 81 which rotates by a predetermined angle for every 20 seconds. If about 180 seconds (20 seconds×9) are required for the reaction between the R1 reagent and the sample, the cuvette containing the R1 reagent and the sample is rotatably transported by 9 pitches after being dispensed with sample. Thus, the trapping antibody (R1 reagent) and the antigen of the sample bind while the cuvette is being rotatably transported.

(R2 Reagent Dispensing Step)

After aspirating the R2 reagent in the reagent container installed in the reagent installing member 60b, the reagent dispensing arm 90b is turned towards the primary reaction member 80a side to discharge the aspirated R2 reagent into the cuvette containing the R1 reagent and the sample incubated for a predetermined time. As shown in FIGS. 5 and 6, the R2 reagent contains magnetic particles that bind to the trapping antibody bound with the antigen in the sample.

(Stirring Step of R2 Reagent and Sample)

The container conveyance section 82 of the primary reaction member 80a then stirs the cuvette containing the R1 reagent, the sample, and the R2 reagent similar to stirring step of R1 reagent and sample described above.

(Incubation Step (Reaction 2 Shown in FIGS. 5 and 6))

The stirred R1 reagent, the sample, and the R2 reagent are then incubated for a predetermined time in the cuvette of the holder 81a of the rotatable table 81. If about 100 seconds (20 seconds×5) are required for the reaction between the trapping antibody (R1 reagent) bound with the antigen of the sample and the magnetic particles (R2 reagent), the cuvette containing the R1 reagent, the sample, and the R2 reagent is rotatably transported by 5 pitches after being dispensed with the R2 reagent. Thus, the magnetic particles (R2 reagent) and the trapping antibody (R1 reagent) bound with the antigen of the sample bind while the cuvette is being rotatably transported.

(Conveying Step from Primary Reaction Member 80a to Primary B/F Separator 100a)

The cuvette containing the incubated R1 reagent, the sample, and the R2 reagent is conveyed to the primary B/F separator 100a by the container conveyance section 82 of the primary reaction member 80a.

(First Washing Step in Primary B/F Separator 100a)

In the present embodiment, the magnetic particles in the cuvette are collected by a magnet arranged on the side of the cuvette, and after inserting a nozzle into the cuvette, the specimen in the cuvette is aspirated to remove unnecessary components other than the magnetic particles and the antigen binding with the magnetic particles through the trapping antibody. However, in the first washing step, some of the unnecessary components sometimes retain at the inner wall of the cuvette with the magnetic particles as if being caught in the magnetic particles attracted to the magnet, and thus it becomes difficult to sufficiently remove the unnecessary components; therefore, a stirring step and a second washing step described below are carried out to sufficiently remove the unnecessary components in the present embodiment.

(Stirring Step in Primary B/F Separator 100a (First Time))

In the present embodiment, washing liquid is supplied into the cuvette performed with the first washing step in the primary B/F separator 100a, and stirring is performed. The unnecessary components caught in the magnetic particles and retained at the inner wall of the cuvette with the magnetic particles then can be dispersed.

(Second Washing Step in Primary B/F Separator 100a (First Time))

In the present embodiment, the magnetic particles in the cuvette stirred in the primary B/F separator 100a are again collected on the magnet side arranged on the side of the cuvette. After collecting the magnetic particles in the cuvette, washing liquid and unnecessary components are discharged.

(Stirring Step in Primary B/F Separator 100a (Second Time))

Furthermore, in the present embodiment, washing liquid is again supplied into the cuvette performed with the first second washing step in the primary B/F separator 100a, and stirring is performed.

(Second Washing Step in Primary B/F Separator 100a (Second Time))

In the present embodiment, the magnetic particles in the cuvette stirred in the primary B/F separator 100a are again collected on the magnet side arranged on the side of the cuvette. After collecting the magnetic particles in the cuvette, washing liquid and slightly remaining unnecessary components are reliably discharged.

Subsequently, similar stirring step and the second washing step are further carried out by two times.

(Conveying Step from Primary B/F Separator 100a to Secondary Reaction Member 80b)

The cuvette in which separation of the unnecessary components and the magnetic particles is performed by the primary B/F separator 100a is gripped by the arm 96a of the conveyance mechanism 96, and conveyed to the holder 83a of the rotatable table 83 of the secondary reaction member 80b, as shown in FIG. 1.

(R3 Reagent Dispensing Step)

After aspirating the R3 reagent in the reagent container installed in the reagent installing member 60a, the reagent dispensing arm 90c is turned towards the secondary reaction member 80b side to discharge a predetermined amount of R3 reagent into the cuvette containing the magnetic particles (R2 reagent) and the antigen of the sample bound through the trapping antibody (R1 reagent). As shown in FIGS. 5 and 6, the R3 reagent contains labeling antibody that binds to the antigen in the sample.

(Stirring Step of R3 Reagent and Sample)

The container conveyance section 84 of the secondary reaction member 80b then stirs the cuvette containing the trapping antibody (R1 reagent), the antigen (sample), the magnetic particles (R2 reagent), and the R3 reagent containing the labeling antibody, similar to the stirring step of R1 reagent and sample described above.

(Incubation Step (Reaction 3 Shown in FIGS. 5 and 6))

The stirred trapping antibody (R1 reagent), the antigen (sample), the magnetic particles (R2 reagent), and the R3 reagent containing the labeling antibody are then incubated for a predetermined time in the cuvette of the holder 83a of the rotatable table 83. If about 220 seconds (20 seconds×11) are required for the reaction between the antigen of the sample and the labeling antibody (R3 reagent), the cuvette containing the trapping antibody (R1 reagent), the antigen (sample), the magnetic particles (R2 reagent), and the R3 reagent containing the labeling antibody is rotatably transported by 11 pitches after being dispensed with the R3 reagent. Thus, the antigen bound with the magnetic particles (R2 reagent) through the trapping antibody (R1 reagent) and the labeling antibody (R3 reagent) bind while the cuvette is being rotatably transported.

(Conveying Step from Secondary Reaction Member 80b to Secondary B/F Separator 100b)

The cuvette 8 containing the incubated trapping antibody (R1 reagent), the antigen (sample), the magnetic particles (R2 reagent), and the R3 reagent containing the labeling antibody is conveyed to the secondary B/F separator 100b by the container conveyance section 84 of the secondary reaction member 80b, similar to the conveying step from the primary reaction member 80a to the primary B/F separator 100a described above.

(First Washing Step, Stirring Step, and Second Washing Step in Secondary B/F Separator 100b)

In the present embodiment, similar to the first washing step, the four stirring steps, and the second washing step in the primary B/F separator 100a described above, the first washing step, four stirring steps, and the second washing step are performed in the secondary B/F separator 100b. Thus, the R3 reagent (unnecessary component) containing the labeling antibody that does not bind with the antigen of the sample can be sufficiently removed. Thereafter, the cuvette containing the specimen including the antigen bound with the labeling antibody removed with unnecessary components is transported in the rotating direction with the rotation of the secondary B/F separator 100b, and conveyed to a position to which it can be conveyed by the container conveyance section 84 of the secondary reaction member 80b.

(Conveying Step from Secondary B/F Separator 100a to Secondary Reaction Member 80b)

The cuvette 8 in which separation of the unnecessary components and the magnetic particles is performed by the secondary B/F separator 100b is again conveyed to the holder 83a of the rotatable table 83 by the container conveyance section 84 of the secondary reaction member 80b.

(R4 Reagent Dispensing Step)

The R4 reagent supply member discharges the R4 reagent (dispersion liquid) in the reagent container (not shown) installed at the lower part of the immune analyzer 1 into the cuvette containing the trapping antibody (R1 reagent), the magnetic particles (R2 reagent), the labeling antibody (R3 reagent), and the antigen of sample.

(Stirring Step of R4 Reagent and Labeling Antibody)

The container conveyance section 84 of the secondary reaction member 80b then stirs the cuvette containing the trapping antibody (R1 reagent), the antigen (sample), the magnetic particles (R2 reagent), the labeling antibody (R3 reagent), and the R4 reagent, similar to the stirring step of R1 reagent and sample described above.

(R5 Reagent Dispensing Step)

The R5 reagent supply member discharges a predetermined amount of R5 reagent containing luminescent substrate in the reagent container (not shown) installed at the lower part of the immune analyzer 1 into the cuvette containing the trapping antibody (R1 reagent), the magnetic particles (R2 reagent), the labeling antibody (R3 reagent), the dispersion liquid (R4 reagent), and the antigen of sample. As shown in FIGS. 5 and 6, the R5 reagent contains luminescent substrate that emits light by reacting with the labeling antibody of the R3 reagent.

(Stirring Step of R5 Reagent and Labeling Antibody)

The container conveyance section 84 of the secondary reaction member 80b stirs the cuvette containing the trapping antibody (R1 reagent), the antigen (sample), the magnetic particles (R2 reagent), the labeling antibody (R3 reagent), the dispersion liquid (R4 reagent), and the R5 reagent containing the luminescent substrate, similar to the stirring step of R1 reagent and sample described above.

(Incubation Step (Reaction 4 Shown in FIGS. 5 and 6))

The stirred trapping antibody (R1 reagent), the antigen (sample), the magnetic particles (R2 reagent), the dispersion liquid (R4 reagent), the labeling antibody, and the R5 reagent containing the luminescent substrate are then incubated for a predetermined time in the cuvette of the holder 83a of the rotatable table 83. If about 420 seconds (20 seconds×21) are required for the reaction between the labeling antibody (R3 reagent) bound to the antigen of the sample and the luminescent substrate (R5 reagent), the cuvette containing the trapping antibody (R1 reagent), the antigen (sample), the magnetic particles (R2 reagent), the labeling antibody (R3 reagent), and the R5 reagent containing the luminescent substrate is rotatably transported by 21 pitches after being dispensed with the R5 reagent. Thus, the reaction between the labeling antibody (R3 reagent) and the luminescent substrate (R5 reagent) proceeds while the cuvette is being rotatably transported.

(Measuring Step)

Subsequently, the cuvette containing the incubated trapping antibody (R1 reagent), the antigen (sample), the magnetic particles (R2 reagent), the labeling antibody (R3 reagent), the dispersion liquid (R4 reagent), and the R5 reagent containing the luminescent substrate is conveyed to the measurement position by the conveyance mechanism section 121 of the detector 120. The light emission amount (amount proportional to the number of photons) generated in the reaction process of the labeling antibody of the R3 reagent and the luminescent substrate of the R5 reagent is acquired with the photo multiplier tube (not shown). The acquired measurement result is transmitted to the personal computer 401 having the control member 400a.

(Discarding Step)

The cuvette containing the measured specimen performed with measurement is conveyed to the position below the aspiration part (not shown) by the conveyance mechanism section 121 of the detector 120. The aspiration part moves downward, aspirates the measured specimen, and empties the cuvette. Thereafter, the conveyance mechanism section 121 of the detector 120 gripping the empty cuvette is turned to be conveyed up to the position corresponding to the discarding hole 130, and thereafter, caused to drop the empty cuvette into the discarding hole 130 by un-gripping to discard the used cuvette into the dust box (not shown) arranged at the lower part of the immune analyzer 1 through the discarding hole 130.

[Measurement Progress Screen Display]

In the present embodiment, the measurement process proceeds as described above, wherein the time required until the end of analysis (analysis remaining time) or the analysis end time that the analysis ends is acquired for each sample, and the time required until the end of analysis for all of the samples by the measurement unit (total analysis remaining time) or the entire analysis end time that the analysis of all of the samples ends is acquired. The analysis remaining time and total analysis remaining time acquired as above are displayed on the display member 400b of the control device 400. Thus, the user can check the analysis remaining time for every sample and can check the total analysis remaining time until the analysis of all of the samples end, and as a result, the time management of analysis for all of the samples in addition to the time management of analysis in units of samples can be easily performed.

Figure 7:
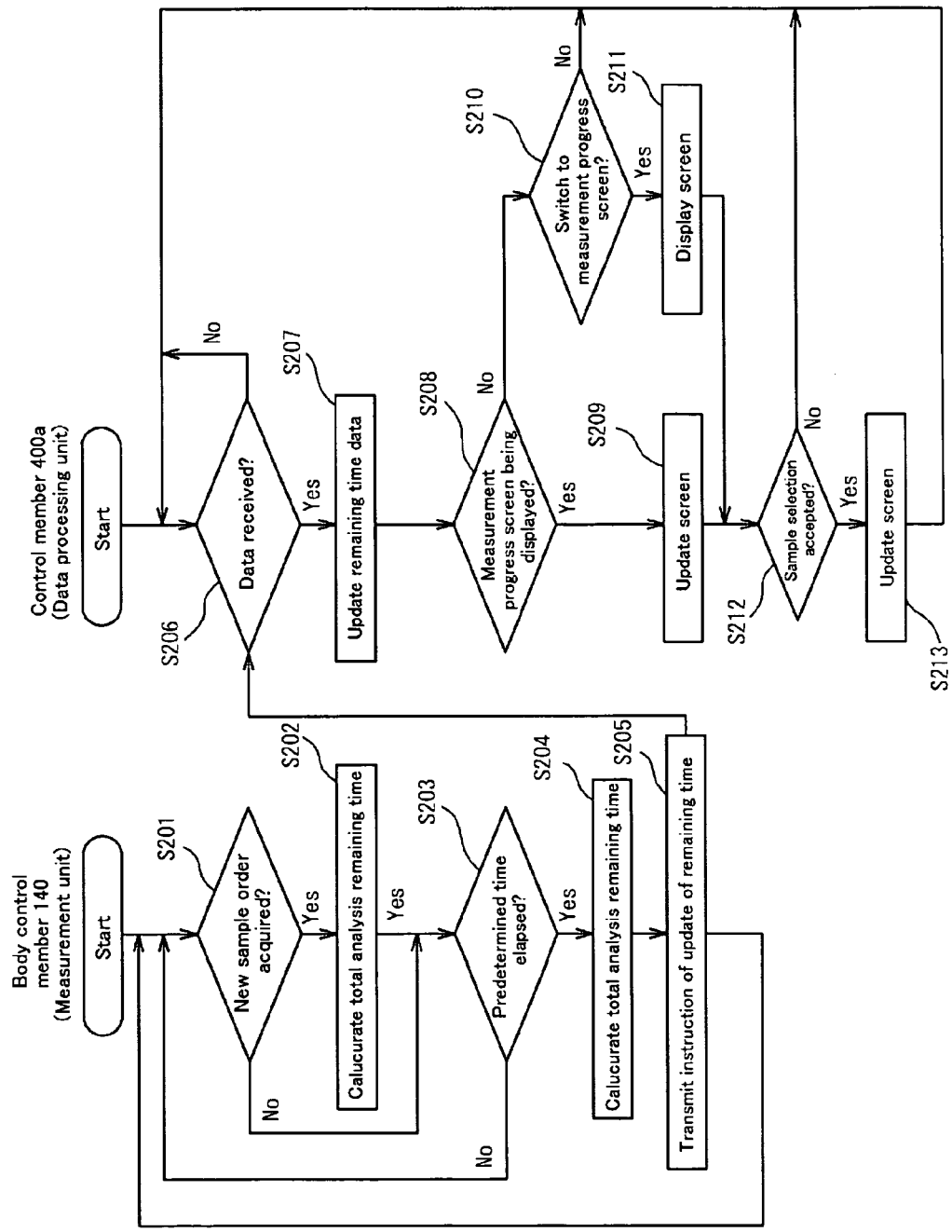
FIG. 7 is a flowchart for updating a total analysis remaining time.

The immune analyzer 1 calculates the total analysis remaining time and the analysis remaining time of each sample, and updates the total analysis remaining time and the analysis remaining time depending on the progress of measurement. First, the updating operation of the total analysis remaining time will be described. FIG. 7 is a view showing a flow for updating the total analysis remaining time. First, in step S201, the body control member 140 determines whether or not an analysis order of a new sample is acquired. That is, whether or not the barcode information of the new sample is read and the analysis order of the relevant sample is acquired is determined. The body control member 140 advances the process to step S202 when determining that the analysis order of the new sample is acquired (Yes), and advances the process to step S203 when determining that the analysis order of the new sample is not acquired (No).

In step S202, the body control member 140 calculates the total analysis remaining time. Specifically, the barcode being specific information for specifying the sample is given to the test tube containing the sample, wherein the time until the analysis of the sample in which barcode is read lastly ends (analysis remaining time of sample in which barcode is read lastly) is calculated in the present embodiment. In the present embodiment, the cuvette dispensed with the sample and the reagent is held by the holder 81a of the rotatable table 81 of the primary reaction member 80a, the holder 83a of the rotatable table 83 of the secondary reaction member 80b, or the like. The rotatable table 81 and the rotatable table 83 are configured so as to rotate by a predetermined angle for every 20 seconds, and each cuvette is performed with operations such as dispensing of reagent, stirring, and incubation at each stopped position. Assuming that the operation at each stopped position is one analyzing step, the sample analysis is performed by executing an analysis sequence including a predetermined number of analyzing steps. Fifty-three analyzing steps exist in the entire analysis sequence (from dispensing of sample to cuvette until end of analysis) in the present embodiment. The total analysis remaining time can be calculated by subtracting the already operated number of steps of the sample in which barcode is read lastly from the number of analyzing steps (fifty-three steps) registered in the apparatus in advance, and multiplying the unit time (20 seconds in the present embodiment) of each analyzing step to the remaining number of analyzing steps.

In step S203, the body control member 140 determines whether or not a predetermined time has elapsed, that is, whether or not one analyzing step has elapsed. The body control member 140 advances the process to step S204 when determining that the predetermined time (20 seconds) has elapsed (Yes), and returns the process to step S201 when determining that the predetermined time (20 seconds) has not elapsed (No).

In step S204, the body control member 140 newly calculates the total analysis remaining time as in step S202.

In step S205, the body control member 140 transmits instruction of updating the remaining time (update of total analysis remaining time) to the control member 400a.

In step S206, the control member 400a determines whether or not a instruction signal of updating the remaining time from the body control member 140 is received. The control member 400a advances the process to step S207 when determining that the instruction signal of updating the remaining time from the body control member 140 is received (Yes).

In step S207, the control member 400a updates the remaining time data. The remaining time data is stored in the RAM 401c of the control member 400a, and the initial value thereof is zero. In step S207, the remaining time data is updated to the remaining time data transmitted from the body control member 140.

In step S208, the control member 400a determines whether or not the measurement progress screen is being displayed on the display member 400b. The control member 400a advances the process to step S209 when determining that the measurement progress screen is being displayed on the display member 400b (Yes), and advances the process to step S210 when determining that the measurement progress screen is not being displayed on the display member 400b (No).

Figure 9:
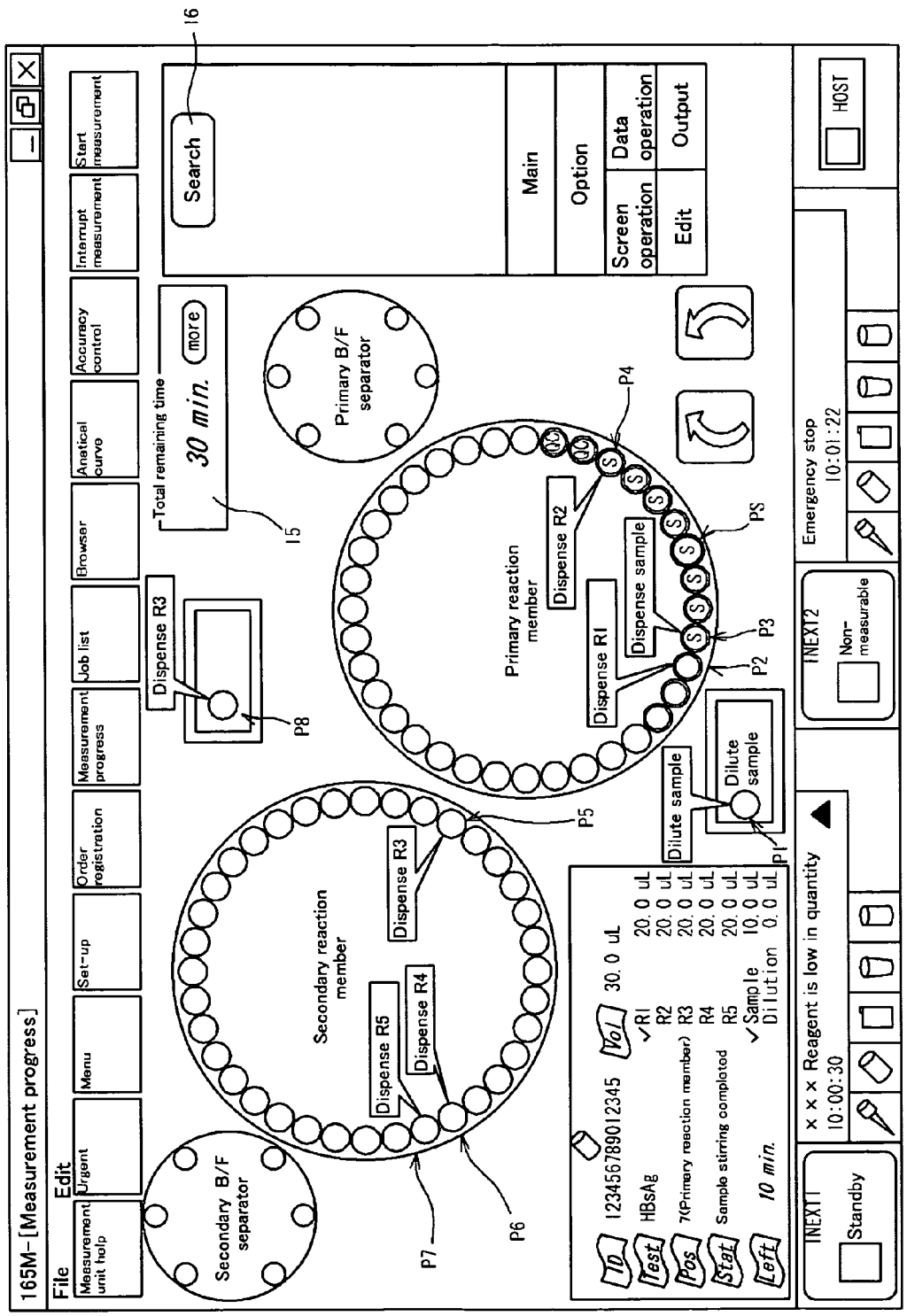
FIG. 9 is a view showing one example of a measurement progress screen.

In step S209, the control member 400a updates the total analysis remaining time displayed on a total analysis remaining time display section 15 at the upper right of the screen shown in FIG. 9. The process then proceeds to step S212.

In step S210, the control member 400a determines whether or not instruction to switch to the measurement progress screen is accepted. The control member 400a advances the process to step S211 when determining that the instruction to switch to the measurement progress screen is accepted (Yes), displays the measurement progress screen on the display member 400b in step S211, and advances the process to step S212. On the other hand, the control member 400a returns the process to step S206 when determining that the instruction to switch to the measurement progress screen is not accepted (No).

The instruction to switch to the measurement progress screen is made when the user selects the "measurement progress icon", whereby the "measurement progress window" is displayed on the display member 400b. The "measurement progress icon" for displaying the measurement progress screen is contained in the basic menu of the screen displayed on the display member 400b after the personal computer 401 is activated, and thus the display itself of the measurement progress screen is possible even before the measurement order is registered, but in this case, the analysis remaining time, the total analysis remaining time, or the like obviously cannot be calculated. Therefore, in reality, the display of the measurement progress screen is instructed after the measurement order is registered or after the dispensing of the sample is started.

FIG. 9 is a view showing one example of the measurement progress screen. In this example, the primary reaction member 80a, the secondary reaction member 80b, the primary B/F separator 100a, the secondary B/F separator 100b, and the detector 120 are displayed on the screen in accordance with the layout of the actual immune analyzer. In FIG. 9, "o" illustrated at the peripheral edge of the primary reaction member 80a or the like is the position of the cuvette containing the sample. The sample is diluted at position P1, and the R1 reagent is dispensed at position P2. Similarly, dispensing of sample, dispensing of R2 reagent, dispensing of R3 reagent, dispensing of R4 reagent, dispensing of R5 reagent, and detection (measurement) are respectively carried out at positions P3 to P8.

The total analysis remaining time is displayed in units of minutes (fractional seconds are rounded up) on the total analysis remaining time display section 15 on the upper right of the screen.

Figure 10:
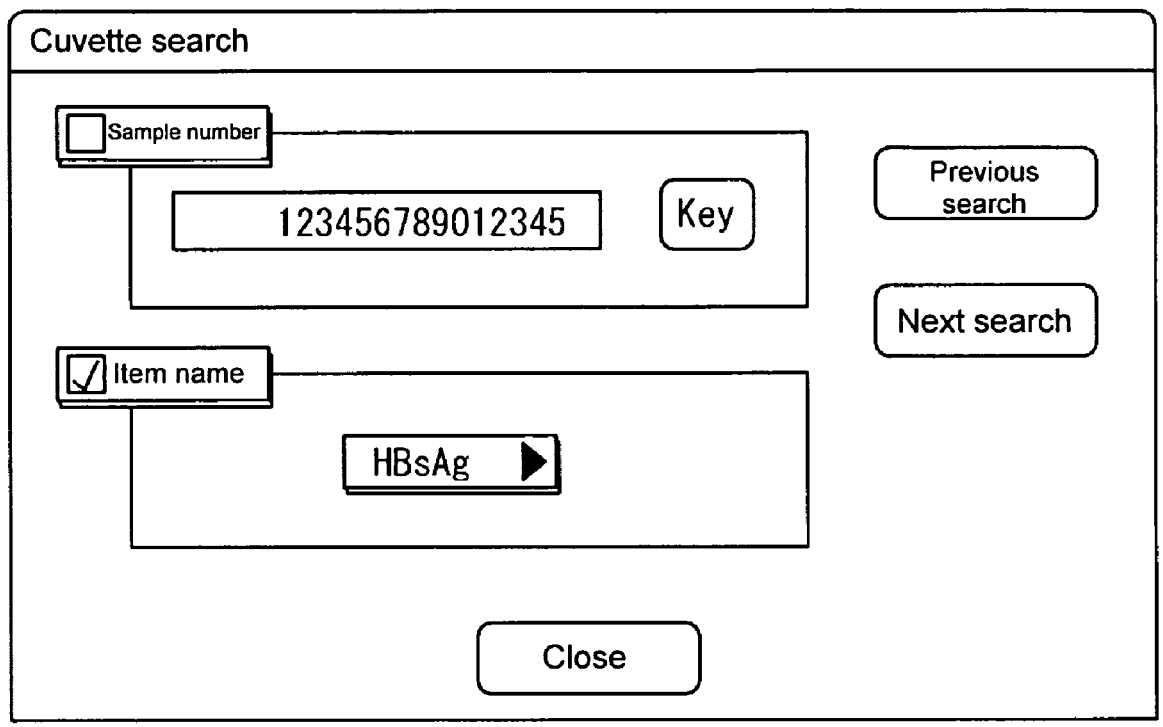
FIG. 10 is a view showing one example of a cuvette search screen.

Various operation buttons are set on the right side of the measurement progress screen. When a "search" button 16 at the top is selected, a "cuvette search window" shown enlarged in FIG. 10 is generated on the measurement progress screen, thereby enabling the input of the sample number. The "cuvette search window" can be skeleton displayed.

In the "cuvette search window", the cuvette can be searched by specifying the sample number or the measurement item. Through such search, the information of the cuvette satisfying the conditions is displayed, and the measurement remaining time and the progress state can be checked. The search condition can be specified by checking the boxes of "sample number" and "item name" (check mark is displayed), and the search is executed by inputting the sample number and/or selecting the measurement item. If the "sample number" is specified as the search condition, the cuvette in which the input sample number and the sample number in measurement order match is searched. If the "item name" is specified as the search condition, the cuvette in which the selected item name and the measurement item in measurement order match is searched. If the "sample number" and the "item name" are selected, search is made with the AND condition. If the candidate is in plurals, the cuvette in which measurement is proceeding mostly (short measurement remaining time) is chosen. In the present embodiment, the sample can also be selected by having the user select through mouse operation etc. the "o" indicating the cuvette (sample) at the peripheral edge of the primary reaction member 80a or the like in FIG. 9. In step S212, the control member 400a determines whether or not the selection of a specific sample where it is desired to know analysis remaining time is accepted by the input described above. The selection of sample in the present embodiment is made in units of cuvette. That is, the sample to be performed with analysis of a plurality of analyzing items is dispensed into a plurality of cuvettes, but in this case, one sample of the samples dispensed to the plurality of cuvettes is selected.

When search is executed, the measurement progress screen is updated, and the "cuvette information window" showing the sample number of the cuvette, the measurement item, the progress state of the measurement, the time (units of minute) until the measurement operation ends (until cuvette is discarded) or the like is displayed on the measurement progress screen (step S213). The control member 400a then returns the process to step S206.

FIG. 11 shows an example of the "cuvette information window", wherein "ID" at the left side of the window indicates the sample number of the searched (selected) sample, and "Test" indicates the measurement item. "Pos" indicates the set position (Position) of the target cuvette. The set position displays the set position number in each mechanism unit (primary reaction member, primary B/F separator, etc.) where the selected cuvette exists, and the relevant mechanism unit. Furthermore, "Stat" indicates the progress state (Status) of measurement of the target cuvette. The progress state is displayed according to the current state of the cuvette shown in table 1. The analysis sequence includes a plurality of analyzing stages such as R1 reagent dispensing, primary B/F separating, detecting, or the like, but which analyzing stage the specified cuvette is currently at can be easily understood by displaying the progress state (status) as in FIG. 11.

TABLE 1

| Name | Zone |
|---|---|
| Cuvette setting complete | Cuvette setting complete to R1 dispensing start |
| R1 dispensing | R1 dispensing start to R1 dispensing end |
| R1 dispensing complete | R1 dispensing end to sample dispensing start |
| Sample dilute solution dispensing | Sample dilute solution dispensing start to sample dilute solution dispensing end |
| Sample dilute solution dispensing complete | Sample dilute solution dispensing end to sample dispensing start |
| Sample dispensing | Sample dispensing start to sample dispensing end |
| Sample dispensing complete | Sample dispensing end to sample stirring end |
| Sample stirring complete | Sample stirring end to R2 dispensing start |
| Sample diluting | Sample dispensing start to sample dilute solution dispensing end to sample dispensing end |
| Sample diluting and stirring complete | Sample dispensing end to sample dilute solution dispensing end to sample stirring end |
| Sample diluting complete | Sample stirring complete (sample dispensing to sample dilute solution dispensing complete) to cuvette discarding |
| R2 dispensing | R2 dispensing start to R2 dispensing end |
| R2 dispensing complete | R2 dispensing end to R2 stirring end |
| R2 stirring complete | R2 stirring end to primary B/F separation start or R3 dispensing start |
| Primary B/F separating | Primary B/F separation start to primary B/F separation end |
| Primary B/F separating complete | Primary B/F separation end to R3 dispensing start |
| R3 dispensing | R3 dispensing start to R3 dispensing end |
| R3 dispensing complete | R3 dispensing end to R3 stirring end |
| R3 stirring complete | R3 stirring end to Secondary B/F separation start |
| Secondary B/F separating | Secondary B/F separation start to secondary B/F separation end |
| Secondary B/F separating complete | Secondary B/F separation end to R4 dispensing start |
| R4 dispensing | R4 dispensing start to R4 dispensing end |
| R4 dispensing complete | R4 dispensing end to R4 stirring end |
| R4 stirring complete | R4 stirring end to R5 dispensing start |
| R5 dispensing | R5 dispensing start to R5 dispensing end |
| R5 dispensing complete | R5 dispensing end to R5 stirring end |
| R5 stirring complete | R5 stirring end to detection start |
| Detecting | Detection start to detection end |
| Detecting complete | Detection end to turbidity detection start |
| Turbidity detecting | Turbidity detection start to turbidity detection complete |
| Turbidity detecting complete | Turbidity detection complete to cuvette discard |

"Left" is displayed with the analysis remaining time, and the time until the target cuvette terminates the measurement operation (cuvette is discarded) is displayed in units of minute (round up seconds). "Vol" at the right side of the window indicates the total remaining amount of liquid in the cuvette of the target cuvette, and the breakdown of the dispensing liquid (R1 to R5 reagents, sample (diluted sample), sample dilute solution). The check mark indicates that dispensing is terminated, in the illustrated example, 10.0 μL of sample (Sample) and 20.0 μL of R1 reagent, being a total of 30.0 μL, are dispensed and contained in the cuvette.

Figure 8:
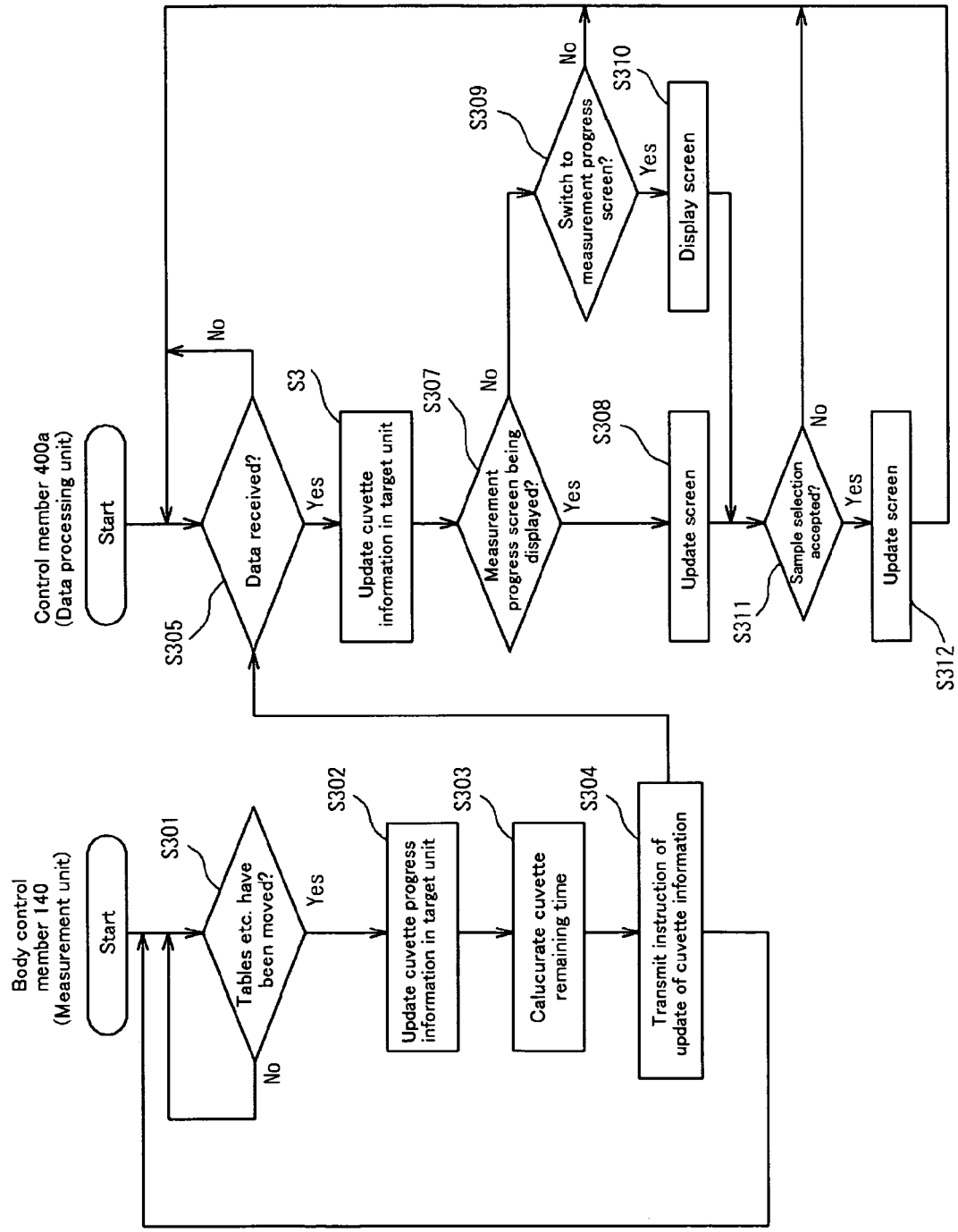
FIG. 8 is a flowchart for updating an analysis remaining time.

The updating operation of the analysis remaining time will now be described. FIG. 8 is a view showing a flow for updating the analysis remaining time.

First, in step S301, the body control member 140 determines whether or not the rotatable table 81 of the primary reaction member 80a and the rotatable table 83 of the secondary reaction member 80b are moved. That is, in the present embodiment, the cuvette is held in each holders of the rotatable table 81 of the primary reaction member 80a, the rotatable table 83 of the secondary reaction member 80b, the primary B/F separator 100a, the secondary B/F separator 100b, and the detector 120, and is moved for every 20 seconds to be performed with operations such as dispensing of reagent and stirring at each stopped position, and determination is made on whether or not the movement to the next stopped position is made in the process of step S301. The body control member 140 advances the process to step S302 when determining that the table or the like are moved (Yes).

In step S302, the body control member 140 updates the progress information of the cuvette in the target unit (the rotatable table 81 of the primary reaction member 80a, the rotatable table 83 of the secondary reaction member 80b, the primary B/F separator 100a, the secondary B/F separator 100b, and the detector 120). The progress information contains position and progress state of the cuvette described above.

In step S303, the body control member 140 calculates the remaining time (analysis remaining time) of each cuvette in the target unit. As described above, though the cuvette is subjected to operations such as dispensing of reagent, and stirring at each stopped position, assuming that the operation at each stopped position is one analyzing step, the sample analysis is performed by executing an analysis sequence including a predetermined number of analyzing steps. Fifty-three analyzing steps exist in the entire analysis sequence (from dispensing of sample to cuvette until end of analysis) in the present embodiment. The analysis remaining time contained in the cuvette information is calculated, for each cuvette, by subtracting the already operated number of steps from the number of analyzing steps (fifty-three steps) registered in the apparatus in advance, and multiplying the unit time (20 seconds in the present embodiment) of each step to the remaining number of steps.

In step S304, the body control member 140 transmits the updated cuvette information (containing cuvette progress information and analysis remaining time information) to the control member 400a.

In step S306, the control member 400a determines whether or not the updated information transmitted from the body control member 140 is received. The control member 400a advances the process to step S306 when determining that the updated cuvette information is received (Yes), and updates the cuvette information in the target unit in step S306.

In step S307, the control member 400a determines whether or not the measurement progress screen is being displayed on the display member 400b. The control member 400a advances the process to step S308 when determining that the measurement progress screen is being displayed on the display member 400b (Yes), and advances the process to step S309 when determining that the measurement progress screen is not being displayed on the display member 400b (No).

In step S308, the control member 400a updates the progress display screen shown in FIG. 9. The process then proceeds to step S311.

In step S309, the control member 400a determines whether or not instruction to switch to the measurement progress screen is accepted. The control member 400a advances the process to step S310 when determining that the instruction to switch to the measurement progress screen is accepted (Yes), displays the measurement progress screen on the display member 400b in step S310, and advances the process to step S311. The control member 400a returns the process to step S305 when determining that the instruction to switch to the measurement progress screen is not accepted (No).

The processes of steps S311 and S312 are similar to the processes of steps S212 and S213, and thus the description thereof will be omitted.

In the embodiment described above, the time required until the analysis of the sample related to the analysis order accepted lastly ends is referred to as "total analysis remaining time", but the present invention is not limited thereto. For instance, "total analysis remaining time" may be the time until the analysis of all of the samples, in which barcode (sample specifying information) for specifying the sample given to the container (or each test tube) containing the sample is input, ends. For another instance, a sample starting to be analyzed by being dispensed into the cuvette, the time until the analysis of all of the dispensed samples ends may be referred to as "total analysis remaining time".

In the embodiment described above, when an analysis of a plurality of measurement item with respect to one sample is carried out, the analysis remaining time until the measurement is calculated as remaining time until the measurement of each sample dispensed to a plurality of cuvettes terminates, the present invention is not limited thereto. For instance, a configuration of calculating the analysis remaining time until the measurement of all of the measurement items terminates for each sample, and displaying such analysis remaining time may be adopted. Specifically, if the sample is allocated to a plurality of aliquots, and each aliquot is contained in the cuvette, the measurement order related to the relevant sample is searched, and the measurement item contained in the measurement order is specified. The analysis remaining time is calculated for the measurement item in which measurement is performed lastly (dispensing of the sample is performed lastly) of the measurement items. Such analysis remaining time calculation process is performed for each sample, and the analysis remaining time of each sample is stored in the RAM 401c or the hard disc 401d. When the user selects through mouse operation "o" indicating the cuvette (sample) displayed at the peripheral edge of the primary reaction member 80a or the like in FIG. 8, the analysis remaining time of the sample is read out and the analysis remaining time is displayed. Thus, in the case of the sample to be performed with measurement on a plurality of items, the user can check the time required until the measurement of all of the measurement items to be measured for the relevant sample ends.

In the present embodiment, a configuration of displaying the analysis remaining time required until the analysis of the selected sample ends and the total analysis remaining time required until the analysis of all of the samples ends is adopted, but is not limited thereto, and a configuration of displaying the analysis end time that the analysis of the selected sample ends and the total analysis end time that the analysis of all of the samples ends may be adopted. Specifically, after calculating the analysis remaining time and the total analysis remaining time in the above manner, the time elapsed by the analysis remaining time from the current time is obtained as the analysis end time, and the time elapsed by the total analysis remaining time from the current time is obtained as the total analysis end time.

In the present embodiment, a configuration of acquiring the analysis remaining time with the time point that the cuvette is discarded as the analysis end time point of the sample is adopted, but is not limited thereto. For instance, a configuration of acquiring the analysis remaining time with the time point that the measurement result is acquired in the detector 120 as the analysis end time point may be adopted, or a configuration of acquiring the analysis remaining time with the time point that the analysis result is displayed on the display member 400b as the analysis end time point may be adopted.

The embodiment disclosed herein is merely illustrative in all aspects and should not be recognized as being restrictive. The scope of the invention is defined by the scope of the claims rather than by the description of the embodiment, and meaning equivalent to the claims and all modifications within the scope is encompassed herein.

For instance, a configuration of calculating the total analysis remaining time and the analysis remaining time of the immune analyzer and displaying the calculated total analysis remaining time and analysis remaining time has been described in the present embodiment, but is not limited thereto, and a configuration of calculating the total analysis remaining time and the analysis remaining time of apparatuses other than the immune analyzer such as gene amplification measurement apparatus, blood coagulation measurement apparatus, and multichannel blood cell analyzer, and displaying the calculated total analysis remaining time and analysis remaining time may be adopted.

Furthermore, a configuration of having the measurement unit and the control device 400 being the data processing unit as separate units has been adopted in the present embodiment, but is not limited thereto, and the control device 400 may be incorporated in the measurement unit to obtain a sample analyzer in which the measurement unit and the data processing unit are integrally configured.

What is claimed is:

1. A sample analyzer comprising:
a control device configured to accept an analysis order that indicates an analysis content;
an analyzing unit, in communication with the control device, configured to perform an analysis sequence on a sample according to the analysis order wherein when a plurality of analysis orders for a plurality of samples are accepted, the analyzing unit is configured to sequentially perform analysis sequences for each of the samples so that one analysis sequence is performed in parallel with another analysis sequence;
a sample specifier for specifying one of a plurality of samples ordered to be analyzed; and
a display that is in communication with the control device;
wherein the control device is configured to determine a first analysis remaining time or a first analysis end time, wherein the first analysis remaining time is a time required until the analyzing unit completes an analysis sequence of specified sample, and the first analysis end time is a time point when the analyzing unit completes an analysis sequence of specified sample,
the control device is further configured to determine a second analysis remaining time or a second analysis end time when the control device accepts a plurality of analysis orders, wherein the second analysis remaining time is a time required until the analyzing unit completes an analysis sequence which is scheduled to be lastly performed among a plurality of analysis sequences for the accepted analysis orders, and the second analysis end time is a time point when the analyzing unit completes an analysis sequence which is scheduled to be lastly performed among a plurality of analysis sequences for the accepted analysis orders;
when the control device accepts a plurality of analysis orders, the control device causes the display to display, a plurality of samples which are ordered to be analyzed, and the second analysis remaining time or the second analysis end time, and when the control device accepts a specification of a sample by the sample specifier, the control device causes the display to display a first analysis remaining time or a first analysis end time of the sample specified by the sample specifier.

2. The analyzer of claim 1 wherein, the analysis order contains analyzing item information that defines one or more measurements to be performed on a sample;

the analyzing unit divides the sample for every instructed analyzing item, and analyzes each sample when the analysis order accepted by control device contains analyzing item information instructing a plurality of analyzing items;

the sample specifier is capable of specifying any one of the samples divided in plurals; and the control device is configured to determine the first analysis remaining time of the divided sample specified by the sample specifier ends or the first analysis end time of the divided sample specified by the sample specifier.

3. The analyzer of claim 1 wherein, the analysis order contains analyzing item information that defines one or more measurements to be performed on a sample;

the analyzing unit divides the sample for every instructed analyzing item, and analyzes each sample when the analysis order accepted by the control device contains analyzing item information instructing a plurality of analyzing items;

the sample specifier is capable of specifying a sample and an analyzing item;

and the control device is configured to determine the first analysis remaining time of the specified analyzing item of the specified sample or the first analysis end time of the specified analyzing item of the specified sample.

4. The analyzer of claim 1 wherein, the analysis order contains analyzing item information that defines one or more measurements to be performed, on a sample;

the analyzing unit divides the sample for every instructed analyzing item, and analyzes each sample when the analysis order accepted by the control device contains analyzing item information instructing a plurality of analyzing items;

and the control device is configured to determine a time required until the analyzing unit completes an analysis sequence of all of the instructed analyzing items of the specified sample as the first analysis remaining time or a time point when the analyzing unit completes an analysis sequence of all of the instructed analyzing items of the specified sample as the first analysis end time.

5. The analyzer of claim 1 wherein,
the analysis sequence includes a predetermined number of analyzing steps; and
the control device is configured to determine the first analysis remaining time or the analysis end time by multiplying a unit time necessary to execute one analyzing step by the number of remaining steps obtained by subtracting the number of already executed analyzing steps from the total number of analyzing steps in the analysis sequence.

6. The analyzer of claim 5 wherein, the control device updates the first analysis remaining time or the first analysis end time displayed every time a predetermined number of analyzing steps elapse.

7. The analyzer of claim 1 wherein, the analysis sequence includes a plurality of analyzing stages; the sample analyzer further comprises an analyzing stage specifier for specifying an analyzing stage being executed by the analyzing unit with respect to the sample specified by the sample specifier; and
the control device causes the display to display the analyzing stage specified by the analyzing stage specifier.

8. The analyzer of claim 1 wherein, the analyzing unit includes a conveyer for conveying a sample, and analyzes a sample with conveying the sample by the conveyer; and
the control device causes the display to display an analyzing unit image illustrating a layout of the analyzing unit, and sample images indicating where samples under analysis locate on the analyzing unit image.

9. The analyzer of claim 1 wherein, the analysis order contains analyzing item information that defines one or more measurements to be performed; and
the control device causes the display to display the analyzing item ordered to be performed on a sample specified by the sample specifier.

10. The analyzer of claim 1, wherein the analyzer further comprises a sample information inputter for inputting sample information for specifying a sample;
the analyzing unit analyzes the sample specified by the sample information inputted by the sample information inputter;
and an analysis sequence for a sample whose sample information is lastly inputted is scheduled to be lastly performed.

11. The analyzer of claim 1 wherein, the analyzing unit includes a dispenser for dispensing a sample, and analyzes the sample dispensed by the dispenser; and
an analysis sequence for a sample which is lastly dispensed by the sample dispenser is scheduled to be lastly performed.

* * * * *